United States Patent [19]

Iemura et al.

[11] 4,430,343
[45] Feb. 7, 1984

[54] BENZIMIDAZOLE DERIVATIVES, PROCESS FOR THE PREPARATION THEREOF AND PHARMACEUTICAL COMPOSITION CONTAINING THE SAME

[75] Inventors: Ryuichi Iemura, Kawanisi; Tsuneo Kawashima, Kobe; Toshikazu Fukuda, Osaka; Keizo Ito, Osaka; Takashi Nose, Nara; Goro Tsukamoto, Toyonaka, all of Japan

[73] Assignee: Kanebo, Ltd., Tokyo, Japan

[21] Appl. No.: 436,032

[22] Filed: Oct. 22, 1982

[30] Foreign Application Priority Data

Nov. 6, 1981 [JP] Japan .................. 56-178804

[51] Int. Cl.³ .................. A61K 31/495; A61K 31/55; C07D 403/02
[52] U.S. Cl. .................. 424/250; 424/273 R; 260/245.6; 544/370
[58] Field of Search .................. 544/370; 260/245.6; 424/250, 273 B

[56] References Cited

U.S. PATENT DOCUMENTS 2,689,853 9/1954 Schenck et al. .................. 260/309.2
3,423,413 1/1969 Priewe et al. .................. 260/268
4,093,726 6/1978 Winn et al. .................. 424/250

FOREIGN PATENT DOCUMENTS 50-126682 10/1975 Japan .................. 544/370

Primary Examiner—Alton D. Rollins
Attorney, Agent, or Firm—Wegner & Bretschneider

[57] ABSTRACT

Novel benzimidazole derivatives of the formula:

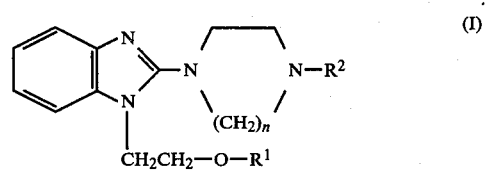

wherein $R^1$ is an alkyl group having 1 to 3 carbon atoms, allyl group, propargyl group, or phenyl group; $R^2$ is hydrogen atom or an alkyl group having 1 to 3 carbon atoms; and n is 2 or 3, or pharmaceutically acceptable acid addition salts thereof, which have excellent antihistaminic activities and are useful as antiallergics for various allergic diseases, and a process for the preparation thereof, and an antihistaminic composition containing the compound as an active ingredient.

10 Claims, No Drawings

BENZIMIDAZOLE DERIVATIVES, PROCESS FOR THE PREPARATION THEREOF AND PHARMACEUTICAL COMPOSITION CONTAINING THE SAME

The present invention relates to novel benzimidazole derivatives, a process for the preparation thereof and a pharmaceutical composition containing the compound as an active ingredient. More particularly, it relates to benzimidazole derivatives of the formula:

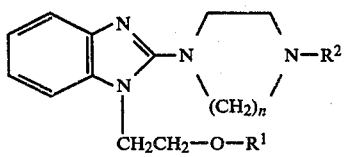
(I)

wherein $R^1$ is an alkyl group having 1 to 3 carbon atoms, allyl group, propargyl group, or phenyl group; $R^2$ is hydrogen atom or an alkyl group having 1 to 3 carbon atoms; and n is 2 or 3, or a pharmaceutically acceptable acid addition salt thereof, a process for the preparation thereof, and a pharmaceutical composition containing the compound useful as antihistaminics.

Histamine is a physiologically active substance which is present in various animals, plants and microorganisms. In human, it is present in a high concentration in skins, mucous membranes of gastro-intestinal tracts, respiratory tissue, particularly in mast cells of these tissues and blood basophils, and by antigen-antibody reaction or contact with or invasion by a certain medicament, high polymer material or toxin, it is released from the cells and acts on $H_1$-receptor to show various physiological activities such as bronchoconstriction, capillary dilatation, increased capillary permeability, or the like, which induce various allergic diseases such as eruption, congestion, inflammation, or the like. In order to prevent or treat such allergic diseases, various medicaments having antagonistic activities against histamine on $H_1$-receptor, i.e. antihistaminics have been developed and actually used.

These conventional antihistaminics are classified by the chemical structure as ethanolamines (e.g. diphenhydramine), ethylenediamines (e.g. tripelennamine), alkylamine (e.g. chlorpheniramine), piperazines (e.g. cyclizine), and phenothiazines (e.g. promethazine). These antihistaminics have such drawbacks that they have week activities, show side-effects such as hypnotic activity even when they have strong activities, or show comparatively high toxicity.

These conventional antihistaminics are characteristic in that they contain a tertiary amino group in the chemical structure. For example, there are known diphenylmethane derivatives, which contain N-substituted piperazinyl group or N-substituted homopiperazinyl group as the tertiary amino group, of the formula:

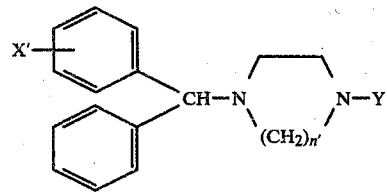
(A)

wherein X' is hydrogen atom, chlorine atom, etc.; Y is an alkyl group or an aralkyl group; n' is 2 or 3, which are different from the compounds of the present invention in the chemical structure thereof.

The compounds of the present invention show superior antihistaminic activities of 10 times or more as much as those of the known antihistaminics of the formula (A), for example, homochlorcyclizine hydrochloride (in the formula (A), X'=chlorine atom, Y=methyl group, n'=3) and show also extremely lower toxicity. The compounds of the present invention are also far superior to the known representative antihistaminics: chlorpheniramine maleate in terms of antihistaminic activities and toxicity.

There are also known some benzimidazole derivatives containing piperazinyl or homopiperazinyl group at 2-position which are structurally similar to the compounds of the present invention. For example, in Japanese Patent Laid Open Application No. 126682/1975, the following compounds having anti-inflammatory and analgesic activities are disclosed:

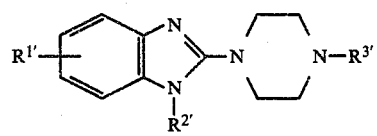
(B)

wherein $R^{1'}$ is hydrogen atom, a halogen atom, a saturated or unsaturated lower alkyl group, a lower alkoxy group or nitro group; $R^{2'}$ is hydrogen atom, a substituted or unsubstituted alkyl group, an alkenyl group, an acyl group, sulfonyl group or an aralkyl group; and $R^{3'}$ is hydrogen atom, a substituted or unsubstituted alkyl group, an alkenyl group, an acyl group, a sulfonyl group, a carbamoyl group, an aryl group, an aralkyl group or a hydroxyalkyl group: specifically, 2-(4-methyl-1-piperazinyl)benzimidazole, 1-methyl-2-(4-methyl-1-piperazinyl)benzimidazole and 1-benzyl-2-(4-methyl-1-piperazinyl)benzimidazole. Moreover, in U.S. Pat. No. 4,093,726, the following compounds having hypotensive activities are disclosed:

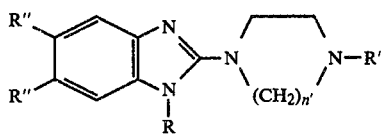
(C)

wherein R is hydrogen atom or methyl group; R' is a $C_{1-6}$ alkyl group, an acyl group, an aryl group, an aroyl group, an alkoxycarbonyl group, tetrahydrofuroyl group, a dialkylaminocarbonyl group or furoyl group; R" is hydrogen atom or methoxy group; and n' is 2 or 3: specifically, 2-(4-isobutyloxycarbonyl-1-piperazinyl)-5,6-dimethoxybenzimidazole, 2-[4-(2-furoyl)-1- homopiperazinyl]-5,6-dimethoxybenzimidazole and 2-(4-methyl-1-piperazinyl)-benzimidazole.

However, these compounds disclosed in the prior art are different from the compounds of the present invention in view of the fact that no ether bond-containing group is present at 1-position of the benzimidazole nucleus. Besides, these literatures disclose merely that the compounds have analgesic, anti-inflammatory or hypotensive activities but do not disclose about antihistaminic activities as in the present invention. In fact, according to experiments of protecting activity of the compounds against histamine-induced lethality, the representative compounds disclosed in the above literatures, 1-methyl-2-(4-methyl-1-piperazinyl)benzimidazole, 1-benzyl-2-(4-methyl-1-piperazinyl)benzimidazole and 2-(4-methyl-1-piperazinyl)benzimidazole showed merely about one severals to one tenth or less of the protecting activity in comparison with that of the compounds of the present invention.

The present inventors have extensively studied on a new type of antihistaminics having excellent antihistaminic activities with low toxicity and high safety. As a result, it has been found that the novel benzimidazole derivatives of the above formula (I) having a specific chemical structure and their pharmaceutically acceptable acid addition salts satisfy the desired requirements.

An object of the present invention is to provide novel benzimidazole derivatives and their pharmaceutically acceptable acid addition salts. Another object of the invention is to provide compounds having excellent antagonistic activities against histamine with low toxicity which are useful for the prophylaxis and treatment of various allergic diseases induced by histamine. A further object of the invention is to provide a process for the preparation of the novel benzimidazole derivatives and their pharmaceutically acceptable acid addition salts. A still further object of the invention is to provide antihistaminics containing these compounds as an active ingredient. These and other objects and advantages of the invention will be apparent to persons skilled in the art by the following description.

The compounds of the present invention are the compounds of the formula (I) as mentioned above and their pharmaceutically acceptable acid addition salts.

The pharmaceutically acceptable acid addition salts include a salt of an organic or inorganic acid, such as maleic acid, fumaric acid, hydrochloric acid, or sulfuric acid.

The compounds (I) of the present invention can be prepared, for example, by the Method A as shown by the following reaction scheme:

METHOD A

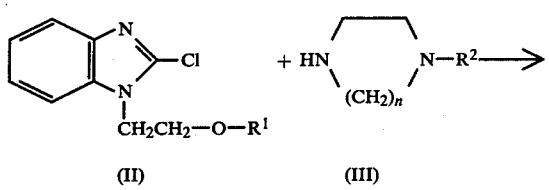

(II)          (III)

-continued

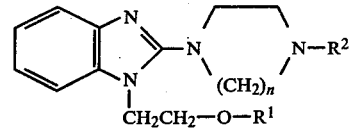

(I)

wherein $R^1$, $R^2$ and n are as defined above.

The starting compounds (II) of the above Method A are also novel compounds and can be prepared by the following method:

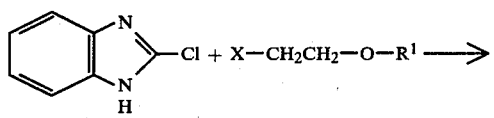

(IV)          (V)

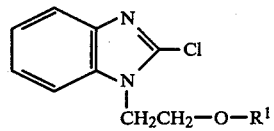

(II)

wherein $R^1$ is as defined above, and X is a halogen atom such as chlorine or bromine atom.

The reaction of the above reaction scheme may be carried out by reacting 1 mole of the 2-chlorobenzimidazole (IV) with the halogen compound (V) of an equimolar or slightly excess amount, usually 1 to 1.5 mole, in an organic solvent in the presence of a base and optionally a catalyst such as potassium iodide. The solvent includes methanol, ethanol, N,N-dimethylformamide, dimethyl sulfoxide, or the like. The base includes an alkali metal (e.g. sodium metal), an alkali metal hydroxide (e.g. sodium hydroxide, potassium hydroxide), an alkali metal hydride (e.g. sodium hydride, potassium hydride), or the like. The base is preferably used in an amount of 1 to 1.5 mole to 1 mole of the 2-chlorobenzimidazole (IV). The reaction temperature is usually in the range of from 0° C. to a boiling point of the solvent, preferably from room temperature to 80° C.

The reaction of the compound (II) with the compound (III) to obtain the compound (I) of the present invention (Method A) is carried out by reacting the compound (II) with an excess amount, usually 2 to 10 equimolar amounts, of the compound (III) without a solvent, or by reacting the compound (II) with an equimolar or excess amount, usually 1 to 2 equimolar amount, of the compound (III) in an organic solvent, preferably in the presence of a base. When the reaction is carried out in a solvent, there is used a solvent such as N,N-dimethylformamide, dimethyl sulfoxide, or N-methyl-2-pyrrolidone. The base includes an aliphatic tertiary amine (e.g. triethylamine) and pyridine, and is preferably used in an amount of 1 to 1.5 equimolar amount to 1 mole of the compound (II). The reaction temperature is in the range of from 100° C. to 130° C. in case of using no solvent and of from 80° C. to a boiling point of the solvent in case of using a solvent.

The compounds (I) of the present invention wherein R² is hydrogen atom may also be prepared by the following method A':

METHOD A'

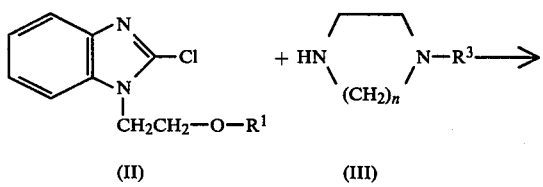

(II)   (III)

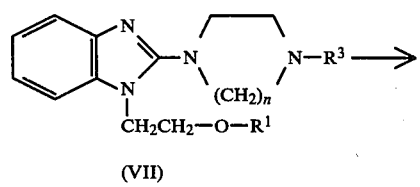

(VII)

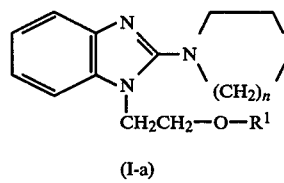

(I-a)

wherein R¹ and n are as defined above, and R³ is a protecting group which can be removed by a catalytic reduction or under an acidic or basic condition.

The protecting group (R³) includes benzyl group which can easily be removed by catalytic reduction, and formyl or ethoxycarbonyl group which can easily be removed under an acidic or basic condition. Removal of the protecting group may be carried out by a conventional method.

Alternatively, the compounds (I) of the present invention wherein R² is an alkyl group having 1 to 3 carbon atoms may be prepared from the compounds (I) wherein R² is hydrogen, i.e. the compounds (I-a) by the following Method A":

METHOD A"

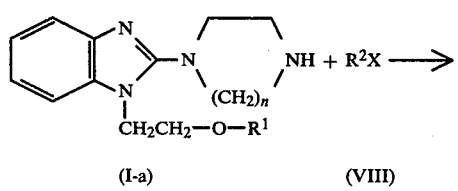

(I-a)   (VIII)

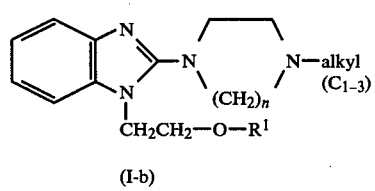

(I-b)

wherein R¹, n and X are as defined above, and R² is an alkyl group having 1 to 3 carbon atoms.

The reaction of the above Method A" can be carried out by reacting the compound (I-a) with an equimolar or slightly excess amount, usually 1 to 1.5 equimolar amount, of the lower alkyl halide (VIII) in an organic solvent in the presence of a base and optionally a catalyst such as potassium iodide. Suitable examples of the solvent are chloroform, methanol and ethanol. The base includes an alkali metal salt (e.g. sodium hydrogen carbonate, potassium carbonate) and an organic base (e.g. triethylamine, pyridine), and the base is usually used in an amount of 1 to 1.5 equimolar amount to 1 mole of the compound (I-a). The reaction temperature is usually in the range of from 0° C. to a boiling point of the solvent.

Alternatively, the compounds (I) of the present invention can be prepared by the Method B as shown by the following reaction scheme:

METHOD B

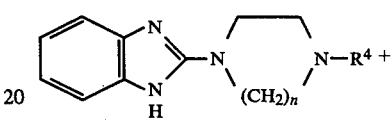

(IX)

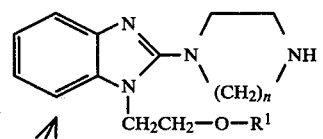

(I-a)

in case of R⁴ = a protecting group
XCH₂CH₂—O—R¹
in case of R⁴ = C₁₋₃ alkyl
(V)

(Removal of R⁴ group)

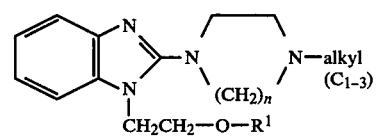

(I-b)

wherein R¹, n and X are as defined above, and R⁴ is an alkyl group having 1 to 3 carbon atoms, or the same protecting group as defined for R³.

In the above Method B, in case of preparing the compounds (I-a) [i.e. R²=hydrogen atom in the formula (I)], the starting compound (IX) wherein R⁴ is a protecting group as defined for R³ is reacted with the halide compound (V), followed by removal of the protecting group in a usual manner. In case of preparing the compounds (I-b) [i.e. R²=an alkyl group having 1 to 3 carbon atoms in the formula (I)], the starting compound (IX) wherein R⁴ is an alkyl group having 1 to 3 carbon atoms is reacted with the halide compound (V).

The starting compound (IX) used in the above Method B may be prepared by reacting 2-chlorobenzimidazole of the formula:

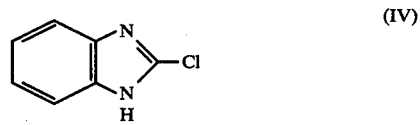

(IV)

with a compound of the formula:

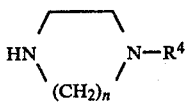

(X)

wherein $R^4$ and n are as defined above, under the same reaction conditions as used in the reaction of the compound (II) and the compound (III) as disclosed hereinbefore.

The reaction of the compound (IX) with the halide compound (V) in the above Method B may be carried out under the same reaction conditions as used in the reaction for the preparation of the starting compound (II) in the above Method A, i.e. the reaction of 2-chlorobenzimidazole with the halide compound (V), but in this case there is preferably used an alkali metal (e.g. sodium metal) or an alkali metal hydride (e.g. sodium hydride, potassium hydride) as the base, and alkali metal hydroxides such as sodium hydroxide and potassium hydroxide are not suitable because it tends to lower the yield of the product when they are used.

The compounds (I) obtained by the above methods may be converted into their acid addition salts by treating them with an inorganic acid (e.g. hydrochloric acid, sulfuric acid) or an organic acid (e.g. maleic acid, fumaric acid) in a usual manner.

The compounds (I) and their pharmaceutically acceptable acid addition salts of the present invention have excellent antagonistic activity against histamine with low toxicity and are useful for the prophylaxis and treatment of various allergic diseases induced by histamine, such as allergoses in respiratory tracts (e.g. allergic rhinitis, allergic inflammatory in respiratory tracts), hay fever, allergic dermatoses (e.g. urticaria, eczema, dermatitis, pruritus, drug eruption, local reactions to insect bite), and allergic conjunctivitis.

The antihistaminic activities and acute toxicities of the compounds of the present invention were tested as follows.

1. Protecting activity against histamine-induced lethality

Test compounds:
(1) Twelve compounds of the present invention as disclosed in Examples 1, 2, 3, 4, 5, 6, 7, 8, 9, 10, 11 and 12 as disclosed hereinafter
(2) Chlorpheniramine maleate (reference compound)
(3) Homochlorcyclizine hydrochloride (reference compound)

Method:
The test was carried out by a method similar to Labell & Tislow method (cf. J. Pharmacol Exp. Ther., 113, 72, 1955). That is, each test compound (in an aqueous solution) or distilled water (as control) was orally administered to Hartley strain male guinea pigs, weighing 250 to 350 g (one group: 6 to 10 animals) which have been fasted for 20 hours. After one hour, histamine (1.1 mg/kg, in a physiological saline solution) was injected to the animals in cephalic vein. After two hours, the number of live guinea pigs was counted, and therefrom $ED_{50}$ of the compounds was calculated according to probit method. In the control group (distilled water was administered), all animals died within 5 minutes after injection of histamine due to dyspnea.

Results:
The results are shown in Table 1 together with the acute toxicity.

2. Acute toxicity ($LD_{50}$)

Test compounds:
The same compounds as used in the above protecting activity against histamine were used.

Method:
The test compounds (in an aqueous solution) were orally administered to ddY strain male mice, weighing 18 to 22 g (one group: 5 to 10 animals) which have been fasted overnight. The mice were observed for one week as to life or death. The $LD_{50}$ was calculated based on the number of dead mice within one week according to Weil's method.

Results:
The results are shown in Table 1.

TABLE 1

| Ex. No. | | Test compounds | | Protecting activity against histamine $ED_{50}$ (mg/kg) | Acute toxicity $LD_{50}$ (mg/kg) |
|---|---|---|---|---|---|
| | n | $R^1$ | $R^2$ | | |
| 1 | 3 | $-CH_2C{\equiv}CH$ | $-CH_3$ | 0.0046 | 990 |
| 2 | 2 | $-CH_2C{\equiv}CH$ | $-CH_3$ | 0.0047 | 818 |
| 3 | 3 | $-CH_2CH_3$ | $-CH_3$ | 0.0047 | 628 |
| 4 | 2 | $-CH_2CH{=}CH_2$ | $-CH_3$ | 0.0058 | 1635 |
| 5 | 2 | $-CH_2CH_3$ | $-CH_3$ | 0.0070 | 1493 |
| 6 | 3 | $-CH_2CH{=}CH_2$ | $-CH_3$ | 0.0088 | 904 |
| 7 | 3 | $-CH_2CH_2CH_3$ | $-CH_3$ | 0.0095 | 884 |
| 8 | 2 | $-CH_2CH_3$ | $-H$ | 0.011 | 2217 |
| 9 | 2 | $-CH_2CH_3$ | $-CH_2CH_3$ | 0.013 | 2639 |
| 10 | 3 |  | $-CH_3$ | 0.014 | 1006 |
| 11 | 2 | $-CH_2CH_2CH_3$ | $-CH_3$ | 0.015 | 2303 |
| 12 | 2 |  | $-CH_3$ | 0.017 | 1110 |
| Chlorpheniramine maleate*[1] | | | | 0.17 | 274 |
| Homochlorcyclizine*[2] hydrochloride | | | | 0.26 | 382 |

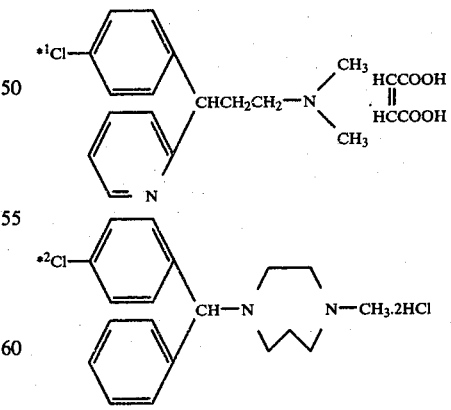

As is clear from the above test results, the compounds of the present invention are far superior to the known anti-histaminic agents such as chlorpheniramine maleate and homochlorcyclizine hydrochloride in the protecting activity against histamine-induced lethality and are also superior to the acute toxicity and hence are superior in safety.

Besides, the conventional antihistaminics have side-effect such as hypnotic activity. For example, according to the experiment of potentiating effect on hexobarbital-induced sleep in mice, homochlorcyclizine hydrochloride showed remarkable potentiating effect in a dose of 25 mg/kg (p.o.), but for example, the compounds of Examples 2, 3, 8 and 9 of the present invention did not show such potentiating effect in a dose of 50 mg/kg (p.o.).

The compounds of the present invention, particularly in the form of a pharmaceutically acceptable acid addition salt thereof, are used for the prophylaxis and treatment of various allergic diseases induced by histamine in conventional preparations for oral administration, injection or external use.

For oral administration, the pharmaceutically acceptable acid addition salt of the present compounds is prepared in the conventional dosage forms, for example, solid preparations such as tablets, granules, fine granules, powders, capsules, and liquid preparations such as syrups. The solid preparations are prepared by using conventional pharmaceutically acceptable carriers such as lactose, starches, crystalline cellulose, talc, etc. Capsules are prepared by encapsulating the fine granules or powders containing the active compounds with an appropriate encapsulating agent. Syrups can be prepared by dissolving or suspending the active compounds of the present invention in an aqueous solution containing sucrose, carboxymethyl cellulose, etc. The preparations for injection can be prepared by dissolving the pharmaceutically acceptable acid addition salt of the present compounds in distilled water or physiological saline solution. Ointments are prepared by using conventional ointment bases such as vaseline, polyethyleneglycol, etc. Intranasal preparations are prepared by dissolving the pharmaceutically acceptable acid addition salt of the present compounds in distilled water or physiological saline solution.

Dose of the present compounds may vary depending on the kinds and severity of diseases, weight and age of patients, etc., but is usually in the range of 0.5 to 5 mg (as a free base) per day in adult in case of oral or injection administration which is divided in two or three times per day. For external use (e.g. in the form of ointment or intranasal preparation), an appropriate amount of the preparations is applied to the area suffered from the diseases.

The present invention is illustrated by the following Examples and Reference Examples but should not be construed to be limited thereto.

REFERENCE EXAMPLE 1

Preparation of
2-chloro-1-[2-($R^1$-oxy)ethyl]-benzimidazoles (II)

In case of 2-chloro-1-[2-(propargyloxy)ethyl]-benzimidazole (Table 2, No. 1), it is prepared as follows.

2-Chlorobenzimidazole (30.0 g) and 2-bromoethyl propargyl ether (41.0 g) are dissolved in N,N-dimethylformamide (300 ml), and thereto is added a 25% aqueous sodium hydroxide (40.0 g), and the mixture is stirred at 60° C. for 4 hours. Water (700 ml) is added to the reaction mixture, and the mixture is extracted with ethyl acetate. The extract is washed with water, dried over anhydrous magnesium sulfate and then concentrated. The resulting residue is distilled under reduced pressure to give 2-chloro-1-[2-(propargyloxy)ethyl]benzimidazole (24.5 g) as a colorless oily substance, b.p. 158°-160° C./1.2 mmHg.

In the same manner as described above except that 2-bromoethyl ethyl ether, 2-bromoethyl allyl ether, 2-bromoethyl n-propyl ether and 2-bromoethyl phenyl ether are used instead of 2-bromoethyl propargyl ether, there are obtained the compounds (Table 2, Nos. 2 to 5), respectively.

TABLE 2

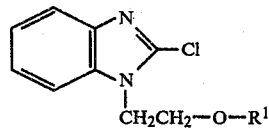

| No. | $R^1$ | Appearance | Boiling point or melting point |
|---|---|---|---|
| 1 | —CH$_2$C≡CH | Colorless oily | 158–160° C./1.2 mmHg |
| 2 | —CH$_2$CH$_3$ | " | 132–133.5° C./0.65 mmHg |
| 3 | —CH$_2$CH═CH$_2$ | " | 149–150° C./2.0 mmHg |
| 4 | —CH$_2$CH$_2$CH$_3$ | " | 128.5–130° C./0.27 mmHg |
| 5 | —⟨phenyl⟩ | Colorless crystals* | 97.5–98.5° C. |

*Recrystallized from benzene-hexane

REFERENCE EXAMPLE 2

Preparation of 2-(4-methyl-1-piperazinyl)benzimidazole (in the formula (IX), $R^4$=CH$_3$, n=2)

A mixture of 2-chlorobenzimidazole (10.00 g) and N-mehylpiperazine (20.00 g) is stirred at 125° C. for 5 hours. A 10% aqueous sodium hydroxide (100 ml) is added to the reaction mixture, and the precipitated crystals are separated by filtration. The filtrate is extracted with chloroform, and the chloroform extract is evaporated to dryness to give the same crystals. The crystals are combined and recrystallized from water-methanol to give 2-(4-methyl-1-piperazinyl)benzimidazole (7.02 g) as colorless needles, m.p. 225°–226° C.

EXAMPLE 1

Preparation of
1-[2-(propargyloxy)ethyl]-2-(4-methyl-1-homopiperazinyl)benzimidazole (Method A)

A mixture of 2-chloro-1-[2-(propargyloxy)ethyl]-benzimidazole (3.70 g) and N-methylhomopiperazine (9.00 g) is stirred at 120° C. for 5 hours. A 5% aqueous sodium hydroxide (50 ml) is added to the reaction mixture, and the mixture is extracted with ethyl acetate. The extract is washed with water, dried over anhydrous magnesium sulfate and then concentrated. The residue is dissolved in a small amount of chloroform and subjected to column chromatography using silica gel (60 g), and then eluted with chloroform-methanol (10:1 by volume). The eluate is concentrated to give a pale yellow oily substance (1.90 g). The pale yellow oily substance is dissolved in ethanol (3 ml) and the solution is added to a solution of fumaric acid (1.50 g) in hot ethanol (18 ml). After the mixture is allowed to cool, the precipitated crystals are separated by filtration and recrystallized from ethyl acetate-ethanol to give 1-[2-(propargyloxy)ethyl]-2-(4-methyl-1-homopiperazinyl)- benzimidazole difumarate (2.14 g) as colorless needles, m.p. 122°–124.5° C.

Elementary analysis for $C_{26}H_{32}N_4O_9$: Calcd. (%): C, 57.34; H, 5.92; N, 10.29; Found (%): C, 57.41; H, 5.94; N, 9.92.

NMR (DMSO-$d_6$, δ ppm): 1.9–2.3 (m, 2H), 2.55–2.75 (4H), 3.0–4.4 (14H), 6.5 (s, 4H), 6.8–7.4 (4H).

EXAMPLE 2

Preparation of 1-[2-(propargyloxy)ethyl]-2-(4-methyl-1-piperazinyl)-benzimidazole (Method A)

In the same manner as described in Example 1 using 2-chloro-1-[2-(propargyloxy)ethyl]benzimidazole (3.00 g), N-methylpiperazine (2.70 g) and fumaric acid (1.52 g), there are obtained crude crystals, which are recrystallized from ethyl acetate-ethanol to give 1-[2-(propargyloxy)ethyl]-2-(4-methyl-1-piperazinyl)benzimidazole.3/2 fumarate (2.80 g) as colorless plates, m.p. 145°–146.5° C.

Elementary analysis for $C_{23}H_{28}N_4O_7$: Calcd. (%): C, 58.47; H, 5.97; N, 11.86; Found (%): C, 57.92; H, 6.06; N, 11.74.

NMR (DMSO-$d_6$, δ ppm): 2.4 (s, 3H), 2.45 (1H), 2.6–2.95 (4H), 3.1–3.45 (4H), 3.7–4.0 (2H), 4.0–4.3 (4H), 6.5 (s, 3H), 6.9–7.5 (4H).

The free base (oil) of the above compound has NMR (CDCl$_3$, δ ppm): 2.3 (s, 3H), 2.35–2.7 (5H), 3.2–3.45 (4H), 3.7–4.3 (6H), 6.95–7.6 (4H).

EXAMPLE 3

Preparation of 1-[2-(ethoxy)ethyl]-2-(4-methyl-1-homopiperazinyl)-benzimidazole (Method A)

In the same manner as described in Example 1 using 2-chloro-1-[2-(ethoxy)ethyl]benzimidazole (3.00 g), N-methylhomopiperazine (3.10 g) and fumaric acid (2.63 g), ther are obtained crude crystals, which are recrystallized from ethyl acetate-ethanol to give 1-[2-(ethoxy)ethyl]-2-(4-methyl-1-homopiperazinyl)benzimidazole.difumarate (3.78 g) as colorless needles, m.p. 141°–143° C.

Elementary analysis for $C_{25}H_{34}N_4O_9$: Calcd. (%): C, 56.17; H, 6.41; N, 10.48; Found (%): C, 56.27; H, 6.29; N, 10.50.

NMR (DMSO-$d_6$, δ ppm): 1.0 (t, 3H), 2.0–2.6 (m, 2H), 2.7 (s, 3H), 3.0–3.9 (12H), 4.0–4.3 (2H), 6.5 (s, 4H), 6.8–7.4 (4H).

The free base (oil) of the above compound has NMR (CDCl$_3$, δ ppm): 1.15 (t, 3H), 1.8–2.25 (m, 2H), 2.4 (s, 3H), 2.6–2.9 (4H), 3.25–3.9 (8H), 4.05–4.35 (2H), 7.0–7.7 (4H).

EXAMPLE 4

Preparation of 1-[2-(allyloxy)ethyl]-2-(4-methyl-1-piperazinyl)benzimidazole (Method A)

In the same manner as described in Example 1 using 1-[2-(allyloxy)ethyl]-2-chlorobenzimidazole (3.00 g), N-methylpiperazine (3.00 g) and fumaric acid (2.16 g), there are obtained crude crystals, which are recrystallized from ethyl acetate-ethanol to give 1-[2-(allyloxy)ethyl]-2-(4-methyl-1-piperazinyl)benzimidazole.3/2 fumarate (3.18 g) as colorless plates, m.p. 161.5°–164° C.

Elementary analysis for $C_{23}H_{30}N_4O_7$: Calcd. (%): C, 58.22; H, 6.37; N, 11.81; Found (%): C, 58.48; H, 6.29; N, 11.99

NMR (DMSO-$d_6$, δ ppm): 2.5 (s, 3H), 2.75–3.15 (4H), 3.15–3.5 (4H), 3.6–3.9 (4H), 4.0–4.3 (2H), 4.8–5.2 (2H), 5.4–5.9 (1H), 6.5 (s, 3H), 6.9–7.4 (4H).

EXAMPLE 5

Preparation of 1-[2-(ethoxy)ethyl]-2-(4-methyl-1-piperazinyl)benzimidazole (method A)

In the same manner as described in Example 1 using 2-chloro-1-[2-(ethoxy)ethyl]benzimidazole (100.0 g), N-methylpiperazine (90.0 g) and fumaric acid (83.0 g), there are obtained crude crystals, which are recrystallized from ethanol to give 1-[2-(ethoxy)ethyl]-2-(4-methyl-1-piperazinyl)benzimidazole.3/2 fumarate (148.0 g) as colorless plates, m.p. 167.5°–168.5° C.

Elementary analysis for $C_{22}H_{30}N_4O_7$: Calcd. (%): C, 57.13; H, 6.54; N, 12.11; Found (%): C, 57.04; H, 6.44; N, 12.02.

NMR (DMSO-$d_6$, δ ppm): 0.95 (t, 3H), 2.45 (s, 3H), 2.7–3.0 (4H), 3.15–3.45 (4H), 3.3 (q, 2H), 3.65 (t, 2H), 4.1 (t, 2H), 6.45 (s, 3H), 6.85–7.4 (m, 4H).

The free base (oil) of the above compound has NMR (CDCl$_3$, δ ppm): 1.15 (t, 3H), 2.35 (s, 3H), 2.45–2.75 (4H), 3.2–3.65 (6H), 3.65–3.9 (2H), 4.0–4.3 (2H), 7.05–7.7 (4H).

EXAMPLE 6

Preparation of 1-[2-(allyloxy)ethyl]-2-(4-methyl-1-homopiperazinyl)-benzimidazole (Method A)

In the same manner as described in Example 1 using 1-[2-(alloyloxy)ethyl]-2-chlorobenzimidazole (4.00 g), N-methylhomopiperazine (4.00 g) and fumaric acid (2.58 g), there are obtained crude crystals, which are recrystallized from ethyl acetate-ethanol to give 1-[2-(allyloxy)ethyl]-2-(4-methyl-1-homopiperazinyl)benzimidazole difumarate (3.85 g) as colorless needles, m.p. 144.5°–146.5° C.

Elementary analysis for $C_{26}H_{34}N_4O_9$: Calcd. (%): C, 57.13; H, 6.27; N, 10.25; Found (%): C, 56.93; H, 6.20; N, 10.32.

NMR (DMSO-$d_6$, δ ppm): 1.8–2.3 (m, 2H), 2.65 (s, 3H), 3.0–3.9 (12H), 3.9–4.3 (2H), 4.7–5.2 (2H), 5.35–5.9 (1H), 6.45 (s, 4H), 6.8–7.35 (4H).

The free base (oil) of the above compound has NMR (CDCl$_3$, δ ppm): 1.8–2.3 (m, 2H), 2.4 (s, 3H), 2.6–2.95 (4H), 3.45–4.3 (10H), 4.9–5.35 (2H), 5.45–6.1 (1H), 6.9–7.55 (4H).

EXAMPLE 7

Preparation of 1-[2-(n-propoxy)ethyl]-2-(4-methyl-1-homopiperazinyl)benzimidazole (Method A)

In the same manner as described in Example 1 using 2-chloro-1-[2-(n-propoxy)ethyl]benzimidazole (2.83 g), N-methylhomopiperazine (3.00 g) and fumaric acid (2.04 g), there are obtained crude crystals, which are recrystallized from ethyl acetate-ethanol to give 1-[2-(n-propoxy)ethyl]-2-(4-methyl-1-homopiperazinyl)benzimidazole difumarate (2.86 g) as colorless needles, m.p. 159.5°–160.5° C.

Elementary analysis for $C_{26}H_{36}N_4O_9$: Calcd. (%): C, 56.93; H, 6.61; N, 10.21; Found (%): C, 57.08; H, 6.73; N, 10.37.

NMR (DMSO-$d_6$, δ ppm): 0.75 (t, 3H), 1.1–1.6 (m, 2H), 1.9–2.4 (m, 2H), 2.7 (s, 3H), 3.25 (t, 2H), 3.2–3.9 (10 H), 4.0–4.3 (2H), 6.5 (s, 4H), 6.95–7.45 (4H).

EXAMPLE 8

Preparation of 1-[2-(ethoxy)ethyl]-2-(1-piperazinyl)benzimidazole (Method A)

In the same manner as described in Example 1 using 2-chloro-1-[2-(ethoxy)ethyl]benzimidazole (5.00 g), piperazine (19.00 g) and fumaric acid (3.19 g), there are obtained crude crystals, which are recrystallized from ethyl acetate-ethanol to give 1-[2-(ethoxy)ethyl]-2-(1-piperazinyl)benzimidazole.3/2 fumarate (2.29 g), as colorless needles, m.p. 167°–169° C.

Elementaly analysis for $C_{21}H_{28}N_4O_7$: Calcd. (%): C, 56.24; H, 6.29; N, 12.49; Found (%): C, 55.96; H, 6.29; N, 12.79.

NMR (DMSO-$d_6$, δ ppm): 0.9 (t, 3H), 3.0–3.5 (10H), 3.6 (t, 2H), 4.1 (t, 2H), 6.4 (s, 3H), 6.85–7.4 (m, 4H).

The free base (oil) of the above compound has NMR (CDCl$_3$, δ ppm): 1.1 (t, 3H), 2.35 (s, 1H), 2.85–3.65 (10H), 3.65–3.9 (2H), 4.0–4.3 (2H), 7.0–7.75 (4H).

EXAMPLE 9

Preparation of 1-[2-(ethoxy)ethyl]-2-(4-ethyl-1-piperazinyl)benzimidazole (Method A)

In the same manner as described in Example 1 using 2-chloro-1-[2-(ethoxy)ethyl]benzimidazole (5.00 g), N-ethylpiperazine (5.10 g) and fumaric acid (2.91 g), there are obtained curde crystals, which are recrystallized from ethyl acetate-ethanol to give 1-[2-(ethoxy)ethyl]-2-(4-ethyl-1-piperazinyl)benzimidazole.3/2 fumarate (5.62 g) as colorless needles, m.p. 134°–135.5° C.

Elementary analysis for $C_{23}H_{32}N_4O_7$: Calcd. (%): C, 57.97; H, 6.77; N, 11.76; Found (%): C, 58.20; H, 6.65; N, 11.90.

NMR (DMSO-$d_6$, δ ppm): 0.95 (t, 3H), 1.1 (t, 3H), 2.2 (q, 2H), 2.7–3.05 (4H), 3.3 (q, 2H), 3.15–3.45 (4H), 3.65 (t, 2H), 4.1 (t, 2H), 6.45 (s, 3H), 6.85–7.35 (m, 4H).

The free base (oil) of the above compound has NMR (CDCl$_3$, δ ppm): 0.9–1.25 (6H), 2.25–2.75 (6H), 3.2–3.65 (6H), 3.65–3.9 (2H), 4.0–4.3 (2H), 7.0–7.75 (4H).

EXAMPLE 10

Preparation of 1-[2-(phenoxy)ethyl]-2-(4-methyl-1-homopiperazinyl)-benzimidazole (Method A)

In the same manner as described in Example 1 using 2-chloro-1-[2-(phenoxy)ethyl)benzimidazole (4.00 g), N-methylhomopiperazine (4.00 g) and fumaric acid (2.65 g), there are obtained crude crystals, which are recrystallized from ethanol to give 1-[2-(phenoxy)ethyl]-2-(4-methyl-1-homopiperazinyl)benzimidazole difumarate (3.50 g) as colorless needles, m.p. 167°–168° C.

Elementary analysis for $C_{29}H_{34}N_4O_9$: Calcd. (%): C, 59.79; H, 5.88; N, 9.62; Found (%): C, 59.74; H, 5.78; N, 9.66.

NMR (DMSO-$d_6$, δ ppm): 1.9–2.4 (2H), 2.75 (s, 3H), 3.05–3.85 (8H), 4.15–4.55 (4H), 6.5 (s, 4H), 6.6–7.5 (9H).

The free base (oil) of the above compound has NMR (CDCl$_3$, δ ppm): 1.75–2.2 (m, 2H), 2.35 (s, 3H), 2.55–2.85 (4H), 3.45–3.75 (4H), 4.15–4.35 (4H), 6.65–7.6 (9H).

EXAMPLE 11

Preparation of 1-[2-(n-propoxy)ethyl]-2-(4-methyl-1-piperazinyl)benzimidazole (Method A)

In the same manner as described in Example 1 using 2-chloro-1-[2-(n-propoxy)ethyl]benzimidazole (3.00 g), N-methylpiperazine (3.00 g) and fumaric acid (2.53 g), there are obtained crude crystals, which are recrystallized from ethyl acetate-ethanol to give 1-[2-(n-propoxy)ethyl]-2-(4-methyl-1-piperazinyl)benzimidazole.3/2 fumarate (3.42 g) as colorless prisms, m.p. 165°–166° C.

Elementary analysis for $C_{23}H_{32}N_4O_7$: Calcd. (%): C, 57.97; H, 6.77; N, 11.76; Found (%): C, 57.79; H, 6.87; N, 11.80.

NMR (DMSO-$d_6$, δ ppm): 0.75 (t, 3H), 1.05–1.65 (m, 2H), 2.5 (s, 3H), 2.7–3.1 (4H), 3.2 (t, 2H), 3.1–3.5 (4H), 3.5–3.85 (2H), 3.95–4.3 (2H), 6.5 (s, 3H), 6.95–7.45 (4H).

EXAMPLE 12

Preparation of 1-[2-(phenoxy)ethyl]-2-(4-methyl-1-piperazinyl)benzimidazole (Method A)

In the same manner as described in Example 1 using 2-chloro-1-[2-(phenoxy)ethyl]benzimidazole (3.00 g), N-methylpiperazine (3.00 g) and fumaric acid (2.14 g), there are obtained crude crystals, which are recrylstallized from ethyl acetate-ethanol to give 1-[2-(phenoxy)ethyl]-2-(4-methyl-1-piperazinyl)benzimidazole.3/2 fumarate (2.99 g) as pale yellow plates, m.p. 152°–153.5° C.

Elementary analysis for $C_{26}H_{30}N_4O_7$: Calcd. (%): C, 61.17; H, 5.92; N, 10.97; Found (%): C, 61.21; H, 5.81; N, 10.96.

NMR (DMSO-$d_6$, δ ppm): 2.5 (s, 3H), 2.7–3.1 (4H), 3.15–3.5 (4H), 4.35 (4H), 6.5 (s, 3H), 6.6–7.55 (9H).

The free base (oil) of the above compound has NMR (CDCl$_3$, δ ppm): 2.3 (s, 3H), 2.35–2.65 (4H), 3.15–3.45 (4H), 4.1–4.4 (4H), 6.55–7.7 (9H)

EXAMPLE 13

Preparation of 1-[2-(ethoxy)ethyl]-2-(4-methyl-1-piperazinyl)benzimidazole (Method B)

2-(4-Methyl-1-piperazinyl)benzimididazole (5.00 g) prepared in Reference Example 2 is dissolved in N,N-dimethylformamide (50 ml) and thereto is added sodium hydride (concentration: 50%) (1.50 g) at room temperature, and the mixture is stirred for 30 minutes. To the mixture is added 2-bromoethyl ethyl ether (4.00 g), and the mixture is stirred at 70° C. for 10 hours. To the reaction mixture is added water (150 ml), and the mixture is extracted with ethyl acetate. The extract is washed with water, dried over anhydrous magnesium sulfate and then concentrated to give a brown oily substance (5.40 g). The brown oily substance is treated with fumaric acid (3.26 g) in the same manner as described in Example 1. The crude crystals thus obtained are recrystallized from ethyl acetate-ethanol to give 1-[2-(ethoxy)ethyl]-2-(4-methyl-1-piperazinyl)benzimidazole.3/2 fumarate (6.31 g) as colorless plates. This product has the same physical properties as those of the product in Example 5.

EXAMPLE 14

Preparation of
1-[2-(ethoxy)ethyl]-2-(1-piperazinyl)benzimidazole
(Method A')

(1) A mixture of 2-chloro-1-[2-(ethoxy)ethyl]-benzimidazole (9.00 g) and N-benzylpiperazine (15.00 g) is stirred at 120° C. for 5 hours. To the reaction mixture is added a 5% aqueous sodium hydroxide (150 ml), and the mixture is extracted with ethyl acetate. The extract is washed with water, dried over anhydrous magnesium sulfate and then concentrated. The resulting residue is dissolved in a small amount of chloroform and subjected to column chromatography using silica gel (160 g) and eluted with chloroform-methanol (20:1 by volume). The eluate is concentrated to give a pale yellow oily substance (14.24 g).

The pale yellow oily substance (2.69 g) is dissolved in ethanol (3 ml), and the solution is added to a solution of maleic acid (1.71 g) in ethanol (9 ml). The precipitated crystals are separated by filtration and recrystallized from ethyl acetate-ethanol to give colorless needles (3.52 g) having the following physical properties, m.p. 144°–145° C.

Elementary analysis for $C_{30}H_{36}N_4O_9$: Calcd. (%): C, 60.39; H, 6.08; N, 9.39; Found (%): C, 60.69; H, 6.12; N, 9.55.

NMR (DMSO-$d_6$, δ ppm): 0.95 (t, 3H), 3.1–3.8 (12H), 3.95–4.35 (4H), 6.0 (4H), 6.9–7.5 (9H).

From the above data, it is identified that the colorless needles having m.p. 144°–145° C. are 1-[2-(ethoxy)ethyl]-2-(4-benzyl-1-piperazinyl)benzimidazole dimaleate, and that the pale yellow oily substance is 1-[2-(ethoxy)ethyl]-2-(4-benzyl-1-piperazinyl)benzimidazole.

(2) The pale yellow oily substance, 1-[2-(ethoxy)ethyl]-2-(4-benzyl-1-piperazinyl)benzimidazole (11.55 g) obtained above, is dissolved in a 80% aqueous acetic acid (100 ml) and thereto is added a 5% palladium-carbon (4.00 g), and the mixture is subjected to catalytic hydrogenation at 60° C. under 3 atm. The reaction mixture is filtered, and the filtrate is concentrated. To the residue is added a 10% aqueous sodium hydroxide (100 ml) and the mixture is extracted with chloroform. The extract is dried over anhydrouds magnesium sulfate and then concentrated to give a brown oily substance (9.77 g). The brown oily substance is dissolved in a small amount of chloroform and subjected to column chromatography using silica gel (100 g) and eluted with chloroform-methanol (7.5:1 by volume). The eluate is concentrated to give a pale yellow oily substance (7.74 g). The pale yellow oily substance is treated with fumaric acid (4.91 g) in the same manner as described in Example 1. The crude crystals thus obtained are recrystallized from ethyl acetate-ethanol to give 1-[2-(ethoxy)ethyl]-2-(1-piperazinyl)benzimidazole.3/2 fumarate (5.06 g) as colorless needles. This product has the same physical properties as those of the product in Example 8.

EXAMPLE 15

Preparation of
1-[2-(ethoxy)ethyl]-2-(1-piperazinyl)benzimidazole
(Method A')

(1) A mixture of 2-chloro-1-[2-(ethoxy)ethyl]-benzimidazole (3.00 g) and N-formylpiperazine (3.50 g) is stirred at 120° C. for 5 hours. To the reaction mixture is added a 5% aqueous sodium hydroxide (50 ml), and the mixture is extracted with ethyl acetate. The extract is dried over anhydrous magnesium sulfate and concentrated. The residue is dissolved in a small amount of chloroform and subjected to column chromatography using silica gel (30 g) and eluted with chloroform-methanol (50:1 by volume). The eluate is concentrated to give a pale yellow oily substance (1.91 g).

The pale yellow oily substance (0.91 g) is dissolved in ethanol (1 ml) and the solution is added to a solution of maleic acid (0.35 g) in ethanol (5 ml). The precipitated crystals are separated by filtration and recrystallized from ethyl acetate-ethanol to give colorless prisms (0.71 g) having the following physical properties, m.p. 113°–114° C.

Elementary analysis for $C_{20}H_{26}N_4O_6$: Calcd. (%): C, 57.40; H, 6.26; N, 13.39; Found (%): C, 57.52; H, 6.22; N, 13.35.

NMR (DMSO-$d_6$, δ ppm): 1.0 (t, 3H), 3.1–3.9 (12H), 4.1–4.35 (2H), 6.1 (s, 2H), 7.0–7.55 (4H), 8.0 (s, 1H).

From the above data, it is identified that the colorless prisms having m.p. 113°–114° C. are 1-[2-(ethoxy)ethyl]-2-(4-formyl-1-piperazinyl)benzimidazole maleate, and that the pale yellow oily substance is 1-[2-(ethoxy)ethyl]-2-(4-formyl-1-piperazinyl)benzimidazole.

(2) The pale yellow oily substance 1-[2-(ethoxy)ethyl]-2-(4-formyl-1-piperazinyl)benzimidazole (1.00 g) obtained above is added to a 20% aqueous sodium hydroxide (3 ml), and the mixture is stirred at 100° C. for 2 hours. To the reaction mixture is added water (10 ml), and the mixture is extracted with ethyl acetate. The extract is dried over anhydrous magnesium sulfate and concentrated to give a brown oily substance (0.83 g). The brown oily substance is treated with fumaric acid (0.53 g) in the same manner as described in Example 1. The crude crystals thus obtained are recrystallized from ethyl acetate-ethanol to give 1-[2-(ethoxy)ethyl]-2-(1-piperazinyl)benzimidazole.3/2 fumarate (0.54 g) as colorless needles. This product has the same physical properties as those of the product in Example 8.

EXAMPLE 16

Preparation of
1-[2-(ethoxy)ethyl]-2-(4-ethyl-1-piperazinyl)benzimidazole (Method A'')

1-[2-(ethoxy)ethyl]-2-(1-piperazinyl)benzimidazole (5.41 g) obtained by the same manner as described in Example 8 is dissolved in ethanol (30 ml) and thereto are added ethyl iodide (3.24 g) and potassium carbonate (1.60 g), and the mixture is stirred at 40° C. for 10 hours. The reaction mixture is filtered, and the filtrate is concentrated. The residue is dissolved in a small amount of chloroform and subjected to column chromatography using silica gel (60 g) and eluted by chloroform-methanol (30:1 by volume). The eluate is concentrated to give a pale yellow oily substance (5.34 g). The pale yellow oily substance is treated with fumaric acid (3.07 g) in the same manner as described in Example 1. The crude crystals thus obtained are recrystallized from ethyl acetate-ethanol to give 1-[2-(ethoxy)-ethyl]-2-(4-ethyl-1-piperazinyl)benzimidazole 3/2 fumarate (6.17 g) as colorless needles. This product has the same physical properties as those of the product in Example 9.

EXAMPLE 17

Preparation of tablets

Compressed tablets containing 1-[2-(propargyloxy)-ethyl]-2-(4-methyl-1-homopiperazinyl)benzimidazole difumarate (the compound of Example 1) (0.5 mg in each tablet) are prepared in the following formulation.

| Ingredients | Amount (g) |
|---|---|
| The compound of Example 1 | 10 |
| Crystalline cellulose | 1610 |
| Lactose | 1600 |
| Carboxymethyl cellulose calcium | 120 |
| Talc | 40 |
| Magnesium stearate | 20 |

The above ingredients are uniformly mixed, and the mixture is tableted in a usual manner to give tablets (each 170 mg).

EXAMPLE 18

Preparation of powders

Powders containing 1-[2-(propargyloxy)ethyl]-2-(4-methyl-1-piperazinyl)benzimidazole.3/2 fumarate (the compound of Example 2) (0.5 mg in each powder pack) are prepared in the following formulation.

| Ingredients | Amount (g) |
|---|---|
| The compound of Example 2 | 5 |
| Lactose | 595 |
| Starch | 400 |

The above ingredients are uniformly mixed, and each 100 mg of the mixture are packed with a package.

EXAMPLE 19

Preparation of capsules

Capsules containing 1-[2-(ethoxy)ethyl]-2-(4-methyl-1-homopiperazinyl)benzimidazole difumarate (the compound of Example 3) (0.5 mg in each capsule) are prepared in the following formulation.

| Ingredients | Amount (g) |
|---|---|
| The compound of Example 3 | 10 |
| Lactose | 2000 |
| Crystalline cellulose | 910 |
| Talc | 60 |
| Magnesium stearate | 20 |

The above ingredients are uniformly mixed, and each 150 mg of the mixture are packed in a hard capsule (grade NO. 3).

EXAMPLE 20

Preparation of syrup

A syrup containing 1-[2-(allyloxy)ethyl]-2-(4-methyl-1-piperazinyl)benzimidazole.3/2 fumarate (the compound of Example 4) (0.2 mg per 1 g of the syrup) is prepared in the following formulation.

| Ingredients | Amount (g) |
|---|---|
| The compound of Example 4 | 0.4 |
| Sucrose | 1200 |
| Ethyl p-hydroxybenzoate | 0.4 |
| Propyl p-hydroxybenzoate | 0.2 |
| Purified water | 799 |

The above ingredients are uniformly dissolved in the purified water with stirring to obtain the syrup.

EXAMPLE 21

Preparation of injection

An injection containing 1-[2-(ethoxy)ethyl]-2-(4-methyl-1-homopiperazinyl)benzimidazole difumarate (the compound of Example 3) (1mg per each ampoule) is prepared in the following formulation.

| Ingredients | Amount |
|---|---|
| The compound of Example 3 | 1 g |
| Physiological saline solution | q.s. |
| Total | 1000 ml |

The compound of Example 3 is completely dissolved in the physiological saline solution, and each 1 ml of the solution is filled in an ampoule in a usual manner.

EXAMPLE 22

Preparation of ointment

An ointment containing 1-[2-(ethoxy)ethyl]-2-(4-methyl-1-homopiperazinyl)benzimidazoledifumarate (the compound of Example 3) (5 mg per 1 g of the ointment) is prepared in the following formulation.

| Ingredients | Amount (g) |
|---|---|
| The compound of Example 3 | 0.5 |
| Polyethylene glycol 4000 | 49.5 |
| Polyethylene glycol 400 | 50.0 |

The above ingredients are mixed well and molten with heating and thereafter cooled to give the ointment.

EXAMPLE 23

Preparation of intranasal preparation

An intranasal preparation containing 1-[2-(ethoxy)ethyl]-2-(4-methyl-1-homopiperazinyl)benzimidazole difumarate (the compound of Example 3) (1 mg per each 1 g of the preparation) is prepared in the following formulation.

| Ingredients | Amount (g) |
|---|---|
| The compound of Example 3 | 1 |
| Ethyl p-hydroxybenzoate | 0.5 |
| Physiological saline solution | 998.5 |

The above ingredients are uniformly mixed to give the intranasal preparation.

What is claimed is:

1. A benzimidazole derivative of the formula:

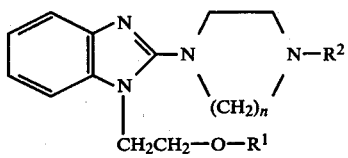

wherein R¹ is an alkyl group having 1 to 3 carbon atoms, allyl group, propargyl group, or phenyl group; R² is hydrogen atom or an alkyl group having 1 to 3 carbon atoms; and n is 2 or 3, or a pharmaceutically acceptable acid addition salt thereof.

2. A compound according to claim 1 which is 1-[2-(ethoxy)ethyl]-2-(4-methyl-1-homopiperazinyl)benzimidazole or a pharmaceutically acceptable acid addition salt thereof.

3. A compound according to claim 1 which is 1-[2-(propargyloxy)ethyl]-2-(4-methyl-1-piperazinyl)benzimidazole or a pharmaceutically acceptable acid addition salt thereof.

4. A compound according to claim 1 which is 1-[2-(ethoxy)ethyl]-2-(1-piperazinyl)benzimidazole or a pharmaceutically acceptable acid addition salt thereof.

5. A compound according to claim 1 which is 1-[2-(phenoxy)ethyl]-2-(4-methyl-1-piperazinyl)benzimidazole or a pharmaceutically acceptable acid addition salt thereof.

6. An antihistaminic composition, which comprises an effective amount of a benzimidazole derivative of the formula:

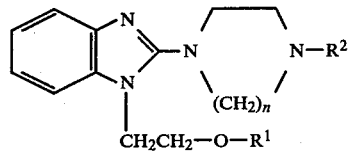

wherein R¹ is an alkyl group having 1 to 3 carbon atoms, allyl group, propargyl group, or phenyl group; R² is hydrogen atom or an alkyl group having 1 to 3 carbon atoms; and n is 2 or 3, or a pharmaceutically acceptable acid addition salt thereof as an active ingredient in admixture with a conventional pharmaceutically acceptable carrier or diluent.

7. The composition according to claim 6, wherein the active ingredient is 1-[2-(ethoxy)ethyl]-2-(4-methyl-1-homopiperazinyl)benzimidazole or a pharmaceutically acceptable acid addition salt thereof.

8. The composition according to claim 6, wherein the active ingredient is 1-[2-(propargyloxy)ethyl]-2-(4-methyl-1-piperazinyl)benzimidazole or a pharmaceutically acceptable acid addition salt thereof.

9. The composition according to claim 6, wherein the active ingredient is 1-[2-(ethoxy)ethyl]-2-(1-piperazinyl)benzimidazole or a pharmaceutically acceptable acid addition salt thereof.

10. The composition according to claim 6, wherein the active ingredient is 1-[2-(phenoxy)ethyl]-2-(4-methyl-1-piperazinyl)benzimidazole or a pharmaceutically acctpable acid addition salt thereof.

* * * * *

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 4,430,343 |
| ISSUED | : | February 7, 1984 |
| INVENTORS | : | Ryuichi Iemura, et al. |
| PATENT OWNER | : | Kanebo, Ltd. |
| PRODUCT | : | EMADINE™ (emedastine difumarate) |

This is to certify that an application under 35 U.S.C. § 156 has been filed in the U.S. Patent and Trademark Office, requesting extension of the term of U.S. Patent No. 4,430,343 based upon the regulatory review of the product EMADINE™ by the Food and Drug Administration. Since it appears that the requirements of the law have been met, this certificate extends the term of the patent for the period of 1,027 days from October 22, 2002, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 19th day of January 2001.

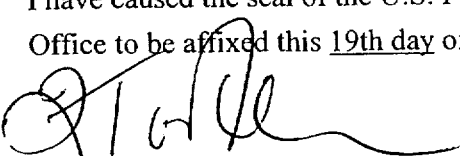

Q. Todd Dickinson
Under Secretary of Commerce for Intellectual Property and
Director of the United States Patent and Trademark Office

UNITED STATES PATENT AND TRADEMARK OFFICE
CERTIFICATE OF CORRECTION

PATENT NO. : 4,430,343
DATED : February 7, 1984
INVENTOR(S) : Ryuichi Iemura et al.

It is certified that error appears in the above-identified patent and that said Letters Patent is hereby corrected as shown below:

<u>Title page,</u>
Item [73], Assignee should read: -- Akzo Nobel N.V. --.

Signed and Sealed this

Twenty-second Day of October, 2002

*Attest:*

JAMES E. ROGAN
*Attesting Officer*         *Director of the United States Patent and Trademark Office*